United States Patent [19]

Heise et al.

[11] Patent Number: 4,954,657

[45] Date of Patent: Sep. 4, 1990

[54] PROCESS FOR THE PREPARATION OF O-NITROPHENETOLE

[75] Inventors: Hartmut Heise, Bad Soden am Taunus; Manfred Hintzmann, Hofheim am Taunus, both of Fed. Rep. of Germany

[73] Assignee: Hoechst Aktiengesellschaft, Frankfurt am Main, Fed. Rep. of Germany

[21] Appl. No.: 267,170

[22] Filed: Nov. 4, 1988

[30] Foreign Application Priority Data

Nov. 7, 1987 [DE] Fed. Rep. of Germany ....... 3737919

[51] Int. Cl.$^5$ .............................................. C07C 43/00
[52] U.S. Cl. ..................................................... 568/584
[58] Field of Search ......................................... 568/584

[56] References Cited

U.S. PATENT DOCUMENTS 2,545,597  3/1951  Ashford et al. .
3,085,113  4/1963  Knowles et al. .
4,454,355  6/1984  Schubert et al. .
4,479,015  10/1984 Sasson et al. .

FOREIGN PATENT DOCUMENTS 902306   8/1962  United Kingdom .
1539183  1/1979  United Kingdom .
2118173  10/1983 United Kingdom .

OTHER PUBLICATIONS

S. G. Riklis, Chem. Abs., 34:54239, (1940).
B. B. Dey et al., J. Scient. Ind. Res. (India), 4, 369–374, (1945).
B. B. Dey et al., J. Scient. Ind. Res. (India) 5B, 25–28, (1946).

*Primary Examiner*—Bruce Gray

[57] ABSTRACT

A process for the preparation of o-nitrophenetole by allowing about 1.05 to about 1.4 mole of ethanol to act on 1 mole of o-nitrochlorobenzene in the presence of a phase-transfer catalyst in approximately 40 to approximately 70 percent by weight alkali metal hydroxide solution at temperatures from about 50° to about 80° C. in such a way that the ethanol concentration in the reaction mixture does not exceed 1.5 percent by weight throughout the course of the reaction.

11 Claims, No Drawings

PROCESS FOR THE PREPARATION OF O-NITROPHENETOLE

DESCRIPTION

A process for the preparation of o-nitrophenetole

The present invention relates to an improved process for the preparation of virtually pure o-nitrophenetole by ethoxylation of o-nitrochlorobenzene.

o-Nitrophenetole is a precursor in the preparation of o-phenetidine which, in turn, is an important intermediate in the preparation of dyestuffs and pharmaceuticals. This is why there has been no lack of attempts in the past to prepare o-nitrophenetole in a straightforward manner and with high yields.

Various processes for the preparation of o-nitrophenetole by ethoxylation of o-nitrochlorobenzene have been described in the literature. According to these, o-nitrochlorobenzene is reacted with ethanol in the presence of alkalis (U.S. Pat. No. 2,545,597, British Pat. No. 902,306, C.A. 34 5423 (1940), U.S. Pat. No. 3,085,113 and J. scient. ind. Res. India 4 (1945) 369 and 5 B (1946) 25).

The essential disadvantage of these known processes is the pronounced occurrence of side reactions. The main byproducts which are formed are azoxy compounds plus o-chloroaniline and o-nitrophenol. Various proposals have been made in the past to suppress the side reactions partially or entirely. Thus, in U.S. Pat. No. 2,545,597 side reactions are prevented by carrying out the ethoxylation in the presence of manganese naphthenate while passing air into the reaction solution.

Attempts have also been made to suppress the formation of azoxybenzenes by carrying out the reaction of o-nitrochlorobenzene with ethanolic sodium hydroxide solution in the presence of metal oxides such as $PbO_2$ or $MnO_2$, as proposed in J. scient. ind. Res. India 4 (1945) 369, 372 and 5 B (1946) 25. Nevertheless, it has never been entirely possible to suppress side reactions leading to, for example, the formation of azoxy compounds, so that the working up of the reaction product had to be followed by additional purification steps. Another disadvantage of this process is that the yields of o-nitrophenetole are usually not above 90% and that approximately complete conversion is not achieved. The unreacted portion of the o-nitrochlorobenzene is in the region of 3 to 6 % of that used, which makes further purification steps necessary during working up.

Attempts have already been made to eliminate these disadvantages by carrying out the ethoxylation of nitrochlorobenzenes in the presence of phase-transfer catalysts. Organic quaternary ammonium salts have been used as catalysts suitable for reactions of this type. Thus, for example, German Offenlegungsschrift 2,634,419 describes the reaction of p-nitrochlorobenzene with ethanol in 50% strength sodium hydroxide solution and in the presence of cetyltrimethylammonium bromide as phase-transfer catalyst. A similar process for the preparation of p-nitrophenetole is to be found in German Offenlegungsschrift 3,120,912. The amounts of catalyst used for this are between 8.5 and 12.5 % by weight of the p-nitrochlorobenzene used, and the yields of p-nitrophenetole are 90 to 95 %, while the remainder is essentially composed of dichloroazoxybenzene.

Whereas the hitherto described known processes in the presence of phase-transfer catalysts related exclusively to the preparation of p-nitrophenetole, German Offenlegungsschrift 3,307,164 describes, besides the preparation of the p isomer, also, for the first time, the ethoxylation of o-nitrochlorobenzene in concentrated sodium hydroxide solution and in the presence of a tetramethylammonium salt as phase-transfer catalyst. It is stated therein that in this process p-nitrophenetole and, analogously thereto, o-nitrophenetole are obtained "completely free of any products of side reactions" and in very high yields of over 97 % based on o-nitrochlorobenzene used. Since experience has shown that the ethoxylation of o-nitrochlorobenzene results in the formation of by-products to a very much greater extent than is the case with the p isomer, one can only be astonished that the process for the preparation of p-nitrophenetole is here simply applied to the o isomer. On repeating the process described in Example 3 of German Offenlegungsschrift 3,307,164 (this is the only example which is directed at the preparation of o-nitrophenetole), despite several attempts and despite exact observance of the process conditions stated therein, it was not possible in any case to obtain a product free of by-products. On the contrary, the o-nitrophenetole prepared as in the said example always contained considerable amounts of by-products of the azoxy type as well as o-chloroaniline, o-nitrophenole and other, unidentified, substances.

Hence the object was to develop a process for the preparation of o-nitrophenetole by ethoxylation of o-nitrochlorobenzene in concentrated alkali metal hydroxide solution and in the presence of a phase-transfer catalyst, which process actually complies with the quality characteristics which are demanded in German Offenlegungsschrift 3,307,164 and which are not achieved by the process described therein.

It has now been found, surprisingly, that o-nitrophenetole can be prepared completely free of azoxy compounds and in high yields by allowing about 1.05 to about 1.4 mole, preferably about 1.1 to about 1.2 mole, of ethanol to act on 1 mole of o-nitrochlorobenzene in the presence of a phasetransfer catalyst in approximately 40 to approximately 70 per cent by weight, preferably about 50 to about 60 % strength, alkali metal hydroxide solution at temperatures from about 50° to about 80° C., preferably from about 65° to about 70° C., in such a way that the ethanol concentration in the reaction mixture does not exceed 1.5 per cent by weight throughout the course of the reaction, and preferably ranges between about 0.2 and about 0.8 per cent by weight. The latter can be achieved by appropriate metering of the ethanol into the reaction solution.

Furthermore, it has been found, surprisingly, that virtually complete conversion of the o-nitrochlorobenzene can be achieved by also metering the phase-transfer catalyst into the reaction mixture. This can be carried out independently of, or expediently together with, the metering in of ethanol.

The addition of the ethanol apart from or together with the phase-transfer catalyst can be carried out in such a way that equal portions are always metered in per unit time or else, corresponding to the course of the reaction, metering in is faster initially and slower towards the end. In this connection, it has proved particularly suitable to meter in catalyst and ethanol together, specifically in such a way that about 60 to about 80 per cent by weight of the amount to be used is rapidly metered in within a particular unit time, followed by the remaining amount in 2- to 4-times the unit time. In this way it is ensured that a particular ethanol concentration is not exceeded throughout the course of the reaction. The actual length of the metering times when the process according to the invention is carried out depends, for example, on the reaction temperature and on the stirring or thorough mixing of the reaction mixture. The only time-determining factor is the progress of the reaction or the ethanol concentration present in the particular reaction mixture, which must be determined in a pilot batch.

The total amount of ethanol used is always in excess, specifically in a ratio of about 1.05 to about 1.4 mole of ethanol per mole of o-nitrochlorobenzene introduced. In this connection, a molar ratio of about 1.1 to about 1.2 mole of ethanol per mole of o-nitrochlorobenzene has proven particularly advantageous.

Particularly suitable phase-transfer catalysts in the process according to the invention are quaternary ammonium salts of the general formula

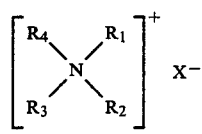

in which $R_1$, $R_2$, $R_3$ and $R_4$ denote identical or different hydrocarbon radicals with a total number of about 10 to about 50 carbon atoms, and X- denotes a halide ion, preferably a chloride or bromide ion, as well as a bisulfate ion ($HSO_4^-$) or hydroxyl ion. The following specific ammonium salts may be mentioned as appropriate: alkylbenzyldimethylammonium chlorides, benzyltributylammonium chloride or bromide, benzyltriethylammonium chloride, benzyltriethylammonium hydroxide, benzyltrimethylammonium chloride, benzyltrimethylammonium hydroxide, ethylhexadecyldimethylammonium bromide, hexadecyltrimethylammonium chloride or bromide, methyltrioctylammonium chloride, tetrabutylammonium bisulfate, tetrabutylammonium hydroxide, tetrabutylammonium bromide or iodide, tetraethylammonium chloride or bromide, tetraethylammonium hydroxide, tetraoctylammonium bromide, tetrapropylammonium bromide and tributylmethylammonium chloride.

Dimethylbenzyl-coconut alkyl($C_{10}$–$C_{18}$)-ammonium chloride with an average molecular weight of 382.5 has proven particularly suitable.

The catalyst can be used both alone and mixed with other phase-transfer catalysts. The catalysts of the said type can be used in the form of aqueous or ethanolic solutions.

The said catalysts can be used in an amount of about 3 to about 15 per cent by weight of the o-nitrochlorobenzene introduced.

The alkali metal hydroxide used is preferably sodium or potassium hydroxide. Mixtures thereof are also suitable. The concentrations used can very in a wide range between about 40 and about 70 per cent by weight, with 50 to 60% strength aqueous solutions being preferred.

When aqueous solutions of the catalyst are used, the water introduced into the reaction must be taken into account when determining the alkali metal hydroxide concentration and, where necessary, compensated by addition of solid sodium or potassium hydroxide. The alkali metal hydroxide is expediently used in an approximately 2- to approximately 6-fold molar excess based on o-nitrochlorobenzene introduced, while in the preferred embodiment an approximately 4- to 5-fold molar excess is used.

The process according to the invention is expediently carried out in such a way that o-nitrochlorobenzene is introduced together with the aqueous alkali metal hydroxide and heated to about 65° to about 68° C. Metering of the solution of catalyst and ethanol is started, while stirring vigorously and cooling cautiously, specifically with a metering rate such that an ethanol concentration of about 0.5 to about 0.6 % in the reaction mixture is not exceeded. After 3/4 of the required amounts of ethanol and catalyst have been metered in a unit time depending on the ethanol content in the reaction mixture, the metering rate is reduced so that the remaining amount runs in in twice the unit time. The reaction temperature of 70° C. should not be exceeded during this. After metering is complete, the mixture is stirred until the concentration of o-nitrochlorobenzene which has not yet reacted has fallen below 1 %, which is generally the case after a total reaction time of 8 to 9 hours.

The examples which follow serve to illustrate the process according to the invention without restricting it thereto.

EXAMPLE 1

A solution of 253.5 g of ethanol and 120 g of dimethylbenzyl-coconut alkyl(C10-C18)-ammonium chloride (50% strength aqueous solution) is pumped into a vigorously stirred mixture of 788 g of o-nitrochlorobenzene, 1600 g of 50% strength sodium hydroxide solution and 260 g of sodium hydroxide at 68° to 70° C., specifically in such a way that during 60 minutes 280 g, and during the following 120 minutes 93.5 g, of the ethanolic catalyst solution enter the reaction mixture. In order to maintain the reaction temperature of 68° to 70° C., cooling is applied at the start of the reaction and heating is applied later. After the running in of the ethanol/catalyst solution is complete, the mixture is stirred at 68° to 70° C. for a further 6 hours. The content of o-nitrochlorobenzene determined by gas chromatography after this is <1 %. After phase separation, 917.5 g of a moist, catalyst-containing product with a purity of 85.8 % is obtained, which corresponds to a yield of 94.2 %. The product is completely free of azoxy compounds.

EXAMPLE 2

A solution of 30 g of tetrabutylammonium bromide in 126.8 g of ethanol is pumped into a vigorously stirred mixture of 392.5 g of o-nitrochlorobenzene, 800 g of 50% strength sodium hydroxide solution and 100 g of sodium hydroxide at 68° to 70° C. in such a way that 120 g of the solution run in during the first 60 minutes and 36.8 g run in during the following 120 minutes. After the running in is complete and after subsequent stirring at 70° C. for 6 hours, the content of o-nitrochlorobenzene is determined by gas chromatography is 0.6 %. After phase separation, 451 g of moist product with a purity of 88.6 % are obtained, corresponding to a yield of 95.6 %.

EXAMPLE 3

20 g of ethanol are metered within 1 hour into a mixture of 78.8 g of o-nitrochlorobenzene, 160 g of sodium hydroxide solution (50% strength) and 6 g of tetrabutylammonium bromide which is heated at 68° to 70° C. and stirred. The remaining 5.4 g of ethanol are then metered in over the course of 2 hours. The conversion achieved after subsequent stirring at 70° C. for 6 hours was 97.4 %. A conversion of 99.2 % was achieved after stirring (70° C.) for 16 hours.

We claim:

1. In the process for the preparation of o-nitrophenetole by the reaction of o-nitrochlorobenzene with ethanol in the presence of a phase-transfer catalyst in an aqueous alkali metal hydroxide solution, the improvement which comprises reacting 1.05 to 1.4 mole of ethanol per mole of o-nitrochlorobenzene in 40 to 70 percent by weight alkali metal hydroxide solution at temperatures ranging from 50° to 80° C., ethanol being present throughout the reaction with the o-nitrochlorobenzene but said ethanol being maintained at a concentration not greater than 1.5 per cent by weight throughout said reaction.

2. The process as claimed in claim 1, wherein the concentration of the ethanol in the reaction mixture ranges between approximately 0.2 to approximately 0.8 per cent by weight.

3. The process as claimed in claim 1, wherein the ethanol is metered into a mixture comprising the o-nitrochlorobenzene and the alkali metal hydroxide solution.

4. The process as claimed in claim 11, wherein the reaction is carried out at temperatures ranging from approximately 65° to approximately 70° C.

5. The process as claimed in claim 1, wherein the alkali metal hydroxide solution is a member selected from the group consisting of aqueous sodium hydroxide solution, potassium hydroxide solution and mixtures thereof.

6. The process as claimed in claim 1, wherein the ethanol and the phase-transfer catalyst are simultaneously, but individually, added to the mixture comprising the o-nitrochlorobenzene and the aqueous alkali metal hydroxide solution.

7. The process as claimed in claim 1, wherein the ethanol and the phase-transfer catalyst are simultaneously, but individually, added in equal portions of each per unit time to the mixture comprising the o-nitrochlorobenezene and the aqueous alkali metal hydroxide solution.

8. The process as claimed in claim 1, wherein the ethanol and the phase-transfer catalyst are added, in different portions of each per unit time, to the mixture comprising the o-nitrochlorobenzene and the aqueous alkali metal hydroxide solution.

9. The process as claimed in claim 1, wherein the ethanol and the phase-transfer catalyst are combined and added to the mixture comprising the o-nitrochlorobenzene and the aqueous alkali metal hydroxide solution at a rate at which 60 to 80% by weight of the total amount of ethanol is initially added during a unit of time, and the remaining amount of ethanol is added during 2 to 4 times said unit of time.

10. The process as claimed in claim 1, wherein the phase-transfer catalyst is a quaternary ammonium salt of the formula

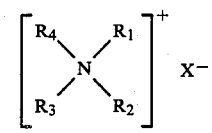

in which $R_1$, $R_2$, $R_3$ and $R_4$ denote identical or different hydrocarbon radicals together having a total number of about 10 to about 50 carbon atoms, and $X^-$ denotes a halide ion, bisulfate ion ($HSO_4^-$) *or hydroxyl ion.*

11. The process as claimed in claim 1, wherein the phase-transfer catalyst is a member selected from the group consisting of dimethylbenzyl-coconut alkyl ($C_{10}$–$C_{18}$)-ammonium chloride, benzyltributylammonium chloride or bromide, benzyltriethylammonium chloride, benzyltriethylammonium hydroxide, benzyltrimethylammonium chloride, benzyltrimethylammonium hydroxide, ethyl-hexadecyl dimethylammonium bromide, hexadecyltrimethylammonium chloride or bromide, methyltrioctylammonium chloride, tetrabutylammonium bisulfate, tetrabutylammonium hydroxide, tetrabutylammonium bromide or iodide, tetraethylammonium chloride or bromide, tetraethylammonium hydroxide, tetraoctylammonium bromide, tetrapropylammonium bromide or tributylmethylammonium chloride.

* * * * *

UNITED STATES PATENT AND TRADEMARK OFFICE
CERTIFICATE OF CORRECTION

PATENT NO. : 4,954,657
DATED : September 4, 1990
INVENTOR(S) : HARTMUT HEISE, ET AL.

It is certified that error appears in the above-identified patent and that said Letters Patent is hereby corrected as shown below:

At Column 3, Line 31, "$HSO_4-$" should read -- $HSO_4^-$ -- .

In Claim 4, at Column 5, Line 24, "claim 11" should read -- claim 1 -- .

In Claim 10, at Column 6, Line 26, "$HSO_r-$" should read -- $HSO_4^-$ -- .

Signed and Sealed this

Twenty-first Day of January, 1992

Attest:

HARRY F. MANBECK, JR.

*Attesting Officer*     *Commissioner of Patents and Trademarks*